United States Patent [19]
McKay

[11] Patent Number: 5,330,455
[45] Date of Patent: Jul. 19, 1994

[54] ENTEROSTOMY APPLIANCE

[76] Inventor: Lester M. McKay, 2804 Buena Vista, Mission Viejo, Calif. 92692

[21] Appl. No.: 868,422

[22] Filed: Apr. 15, 1992

[51] Int. Cl.$^5$ ............................................... A61F 5/44
[52] U.S. Cl. ................................. 604/339; 604/345; 604/332
[58] Field of Search .................. 446/48; 604/332–345; 336/192

[56] References Cited

U.S. PATENT DOCUMENTS

| | | | |
|---|---|---|---|
| 1,083,350 | 1/1914 | Davis | 277/207 X |
| 2,314,724 | 3/1943 | Marsan | 604/338 |
| 3,039,465 | 6/1962 | Berger | 604/338 |
| 3,076,458 | 2/1963 | Mason | 604/339 |
| 3,740,685 | 6/1973 | Fisher | 336/192 |
| 4,132,029 | 1/1979 | Thompson et al. | 446/48 |
| 4,559,048 | 12/1985 | Steer | 604/338 |

FOREIGN PATENT DOCUMENTS 2234885  1/1975  France ................. 604/338

*Primary Examiner*—Randall L. Green
*Assistant Examiner*—Rob Clarke
*Attorney, Agent, or Firm*—Dalton L. Truluck

[57] ABSTRACT

An enterostomy appliance which can be easily and rapidly applied and removed and which is capable of achieving a high quality, completely reliable, fluid-tight seal with the wearer's skin. The appliance does not require adhesive or other sealing medium to effect the seal with the wearer's skin. Also, the appliance is nonirritating to the skin and can be quickly manipulated away from the skin to release flatus without removing clothing. The appliance includes a pouch or bag for receiving discharge from the stoma, an elastomeric sealing ring with a specially constructed sealing surface for establishing the fluid-tight seal with the skin in the area immediately surrounding the stoma, an assembly base for carrying the pouch and sealing ring, and an adjustable elastic belt for encircling the torso and maintaining the pouch, sealing ring and assembly base in proper position on the wearer's body.

26 Claims, 5 Drawing Sheets

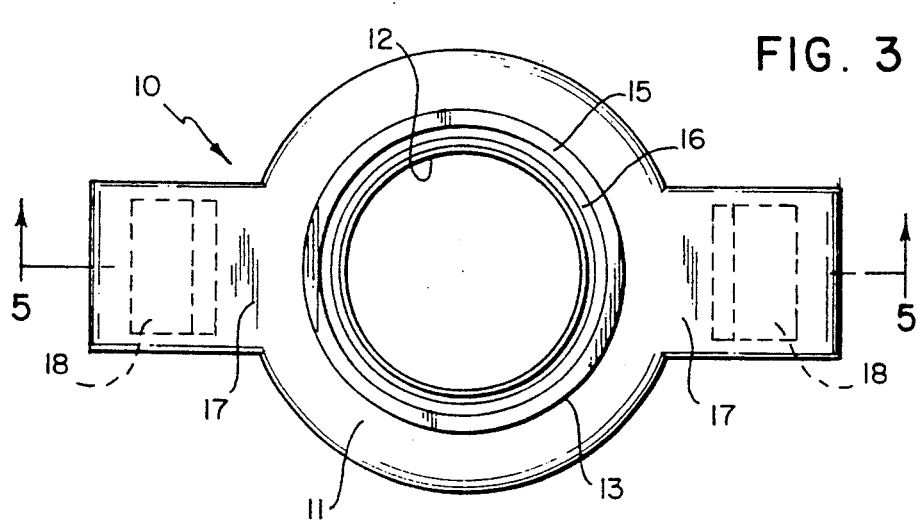
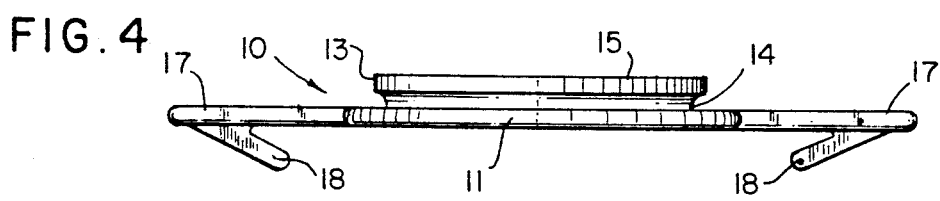
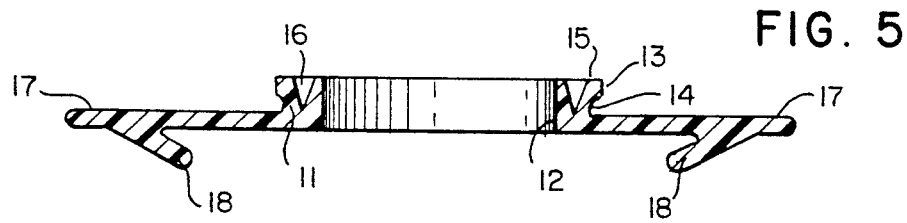
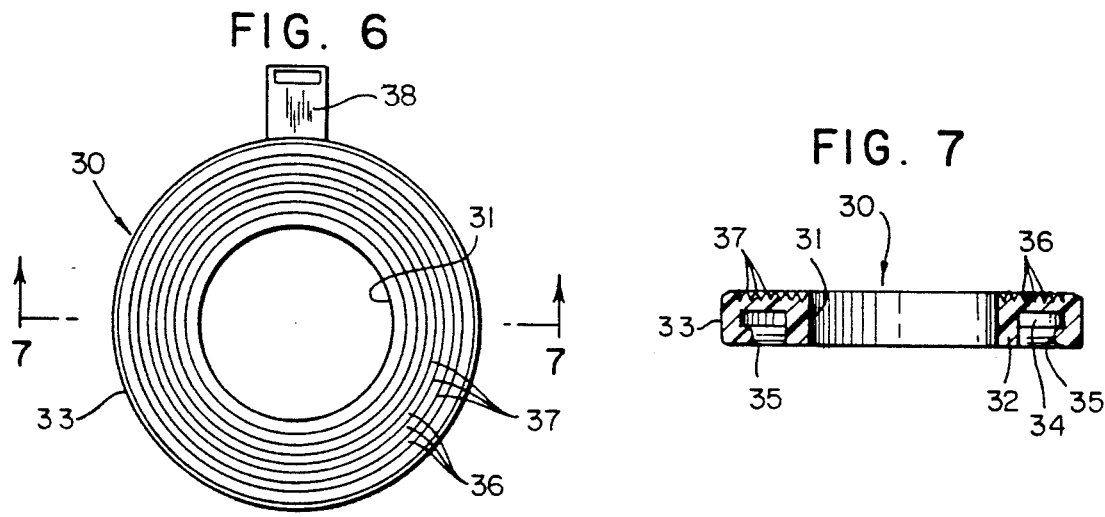

ENTEROSTOMY APPLIANCE

FIELD OF THE INVENTION

This invention relates in general to a surgical appliance to be worn by a patient following a colostomy, an ileostomy, or a cecostomy, these surgical procedures all falling under the general term, enterostomy. More particularly, the invention relates to an improved enterostomy appliance that includes a pouch or bag to be placed in position over an enterostomy opening, i.e., stoma, formed in the patient's abdominal wall to receive feces or other effluent discharged from the body through the opening. The invention especially concerns an improved sealing member for creating a fluid-tight seal with the wearer's body in the area immediately surrounding the stoma without causing irritation to the skin, and improved constructions which hold the enterostomy pouch or bag securely in place so that leakage is avoided and yet allow the pouch to be readily removed when necessary and replaced by a clean, empty one. In addition, the sealing member is so constructed that gas can be released from the pouch easily and without removing the wearer's clothing.

BACKGROUND OF THE INVENTION

Many occasions arise in the treatment of patients by members of the medical profession when it becomes necessary to perform a surgical procedure or operation known as an enterostomy; that is, the surgical formation of an artificial anus by making an opening from the colon, ileum, or cecum through the abdominal wall. Examples of such occasions are in the treatment of ulcerative colitis or in the case of a cancerous colon or cancer of the rectum. The surgical procedure (enterostomy) is more specifically termed a colostomy when the opening is formed from the colon, an ileostomy when the opening is formed from the ileum, and a cecostomy when the opening is formed from the cecum. In each instance, however, the artificial opening thus created in the abdominal wall is uniformly termed a stoma.

Subsequent to an enterostomy, it is necessary to provide a surgical appliance known as an enterostomy appliance in position around the stoma to receive excrement or other effluent discharged from the body through the stoma. Depending upon the particular surgical procedure involved, the appliance may be termed a colostomy appliance, an ileostomy appliance, or a cecostomy appliance, but it is to be understood that the appliance forming the subject matter of this invention is the same regardless of the particular one of these three names by which it is called or the previous particular surgical procedure performed which has necessitated its use. In other words, the same appliance constructed in accordance with the teachings of this invention may be employed at the site of the stoma whether the operation preceding its need was a colostomy, an ileostomy or a cecostomy.

There are numerous requirements which must be met to achieve a completely satisfactory enterostomy appliance. For example, the appliance must be easy for the wearer to attach, and equally easy to remove when necessary for the purpose of installing a clean, empty pouch. In addition, it is essential that the appliance be capable of maintaining a fluid-tight seal with the body at all times while being worn yet capable of being manipulated to release gas when necessary. Also, the appliance must be non-irritating to the skin of the wearer and otherwise comfortable to the wearer at all times. Further, the appliance must be formed and dimensioned so that it does not protrude unduly such that it is noticeable to others in the company of the wearer. Still further, the appliance must be designed so that installation and removal of the pouch both entail very simple procedures which can be executed quickly by the user and do not require great manual dexterity. Of course, the appliance must be completely sanitary.

Although surgical appliances of the type here under concern have long been known, and many designs and varieties exist in the prior art, none has been completely successful in fulfilling all of the above-mentioned requirements. Hence, there has been a long-felt need to attain an enterostomy appliance which meets all of the foregoing requirements and at the same time is economical both from a manufacturing standpoint and to the purchaser.

DISCUSSION OF THE PRIOR ART

As mentioned previously, in spite of the fact that enterostomy appliances have long been known and are available in many styles, all such appliances suffer from one or more deficiencies, thus rendering them unsuitable or undesirable for one reason or another.

One of the most notable deficiencies of prior art enterostomy appliances is their inability to establish an efficacious seal around the stoma in an efficient and simple manner and without causing irritation to the body tissue in the vicinity where they are placed. Many sealing members of enterostomy appliances rely on the use of adhesives for creating the necessary seal. In fact, the utilization of an adhesive is probably the most universally employed expedient for establishing a seal around the stoma. U.S. Pat. No. 4,559,048 to Steer mentions adhesive for this purpose at column 4, lines 19-28 therein. Many other patents likewise teach the use of adhesives. However, the use of adhesive is undesirable because in just a short time it causes irritation to patients with sensitive and tender skin. Even with patients whose skin is not so sensitive, adhesive usually causes irritation after prolonged use. Moreover, an adhesive may give rise to an allergic reaction.

Another technique in the prior art that has been utilized in an attempt to attain a satisfactory seal around the stoma is disclosed in U.S. Pat. No. 3,076,458 to Mason. That technique employs an annular member 10 with a plurality of outwardly extending projections in the form of continuous concentric circular ribs 48 which embed themselves in the skin surrounding the enterostomy opening. However, again not only may such projections cause severe irritation to the skin, but also projections of this sort generally prove to be uncomfortable to the wearer. The member 10 of Mason in addition to having the projecting ribs 48 is tapered or otherwise contoured at the body-confronting face to complement the body contour at the enterostomy opening. This is a distinct disadvantage of the Mason device because the body contour varies at different areas of the abdominal wall and therefore differently shaped members are needed depending on the location of the enterostomy opening. In other words, a single member cannot be manufactured for use at all sites on the body but, rather, several different members must be fabricated. This increases manufacturing costs, introduces inventory problems, and produces other apparent disadvantages. Moreover, in spite of the attributes promoted by Mason in his specification for such structure, the tapering or other contouring of the body-confronting face of his part 10 causes the body to conform to the shape of the appliance rather than, as in the instant invention, the appliance to adapt to the natural shape of the body. As a result, there inevitably will be instances when only a portion of the body-confronting face of the part 10, perhaps only the innermost concentric rib 48 thereof, will actually engage the skin. In such instances the desired seal will be inadequate and leakage will occur.

Still a further artifice for effecting a seal around the stoma is by the use of a sealing member having a single groove or several grooves in the body-confronting face thereof each of which is so constructed as to act as a suction compartment in the manner of a common vacuum cup or suction cup. Examples of this artifice are shown in U.S. Pat. Nos. 2,314,724 to Marsan and 3,039,465 to Berger as well as in French patent 2,234,885 to Velasco et al. Note in particular groove 11 (FIG. 6) in Marsan, grooves 18 and 20 in Berger, and groove 17 in Velasco et al. The use of a groove or grooves in a sealing member to create a vacuum or suction effect is unacceptable because movements of the wearer's body inescapably will result in slight shifting of the sealing member with the resultant loss of vacuum or suction and the consequent failure of the seal.

In addition to the failure to effect a satisfactory seal, the appliances of the prior art also suffer from the drawback of lacking a satisfactory construction for affixing the pouch so that it can be attached and detached quickly and easily and so that it always remains in proper position during use.

Other known deficiencies of prior art enterostomy appliances exist, but the specific examples just given are sufficient to point to the need for improvement in such appliances.

OBJECTS AND SUMMARY OF THE INVENTION

It is the purpose of this invention to provide an entirely satisfactory enterostomy appliance which is devoid of the drawbacks of the prior art appliances while at the same time being simple to use, effective for the function for which it is intended, and economical to produce.

One object of the invention is to provide an appliance of the above nature having a novel construction of a receiving pouch and retainer elements for holding the pouch which will be comfortable to the wearer, completely sanitary, and which will minimize the inconveniences, discomforts, and fears of leakage by enterostomy appliance wearers.

A second object of the invention is to provide a condition in which the receiving bag or pouch will be held in a comfortable, snug position both by an adjustable elastic belt surrounding the torso and by the unique configuration of the contact surface of the appliance, which creates a non-skid condition between the appliance and the skin area around the stoma or artificial anus.

A third object of the invention is to provide an enterostomy appliance which is flexible enough that it will immediately respond to body or muscle movements yet is firm enough to maintain a leakproof contact between the appliance and the wearer.

A fourth object of the invention is to provide an appliance which enables the wearer to release flatus, gas, which is collected in the pouch without removing the clothing.

A fifth object of the invention is to provide an appliance which does not require adhesive to hold it correctly in place over the stoma in sealing relationship with the skin.

A sixth object of the invention is to provide an appliance which can be removed instantly in case of emergency yet requires no buckles or other similar fasteners to hold it in proper place.

A seventh object of the invention is to provide an appliance pouch which can be readily changed by the user yet is configured for attachment to other parts of the appliance in a manner which prevents it from becoming accidentally dislodged.

These and other objects are accomplished by the enterostomy appliance constructed as summarized next below.

Briefly, the enterostomy appliance of the invention consists of four main parts: namely, a pouch or bag for receiving discharge from the stoma, a sealing ring (also termed a stoma ring) for establishing a seal with the skin in the area immediately surrounding the stoma, an assembly base for carrying the pouch and sealing ring, and an adjustable elastic belt for encircling the torso and maintaining the pouch, assembly base, and sealing ring in proper position on the wearer's body. In one embodiment an O-ring is employed as an additional part in conjunction with the open end of the pouch. Except for the top portion thereof, the pouch otherwise is of common construction, as is the adjustable elastic belt. On the other hand, the top portion of the pouch, the assembly base, and the sealing ring are of unique construction and it is these specially constructed novel parts which are responsible for the attainment of a fully satisfactory enterostomy appliance and for the accomplishment of the objects of the invention enumerated hereinabove.

With reference to the accompanying drawings, the invention is now set forth in such clear, concise, and exact terms as to enable anyone skilled in the surgical appliance art to make and use the same.

BRIEF DESCRIPTION OF THE DRAWINGS

FIG. 3 is a top plan view of the assembly base.

FIG. 4 is a side view of the assembly base.

FIG. 5 is a cross-sectional view of the assembly base taken along line 5—5 of FIG. 3.

FIG. 6 is a top plan view of the sealing ring.

FIG. 7 is a cross-sectional view of the sealing ring taken along the line 7—7 of FIG. 6.

DETAILED DESCRIPTION OF THE INVENTION

Figure 1:
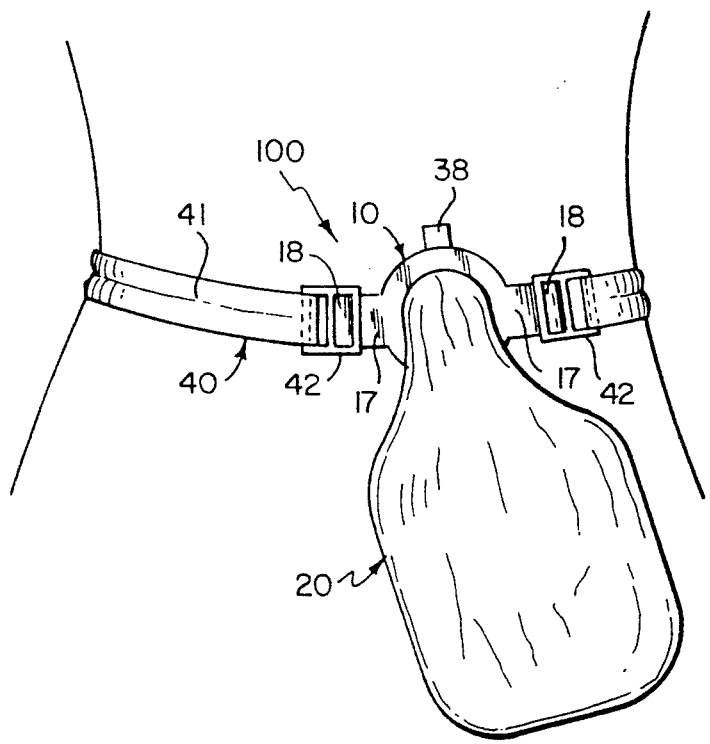
FIG. 1 is an elevational view of the complete enterostomy appliance in position at a typical location on the abdominal wall of the human body.

Referring first to FIG. 1, there is illustrated the enterostomy appliance of the invention, designated in its entirety by the numeral 100, in place on a patient having a left frontal stoma about mid-waist. It is to be understood, however, that the position of the stoma on a patient may vary depending upon such factors as whether the surgical procedure which was performed was a colostomy, an ileostomy, or a cecostomy, and therefore the specific position depicted in FIG. 1 is merely exemplary. Looking also to FIG. 2, the appliance 100 can be seen to consist of four main parts: an assembly base 10 to which the other parts are attached, a pouch or bag 20 for receiving feces or other effluent discharged through the stoma, a sealing ring or stoma ring 30 for establishing a leakproof seal with the skin in the area immediately surrounding the stoma, and an adjustable elastic belt 40 for encircling the torso and maintaining the other parts in proper position on the patient's body.

Figure 2:
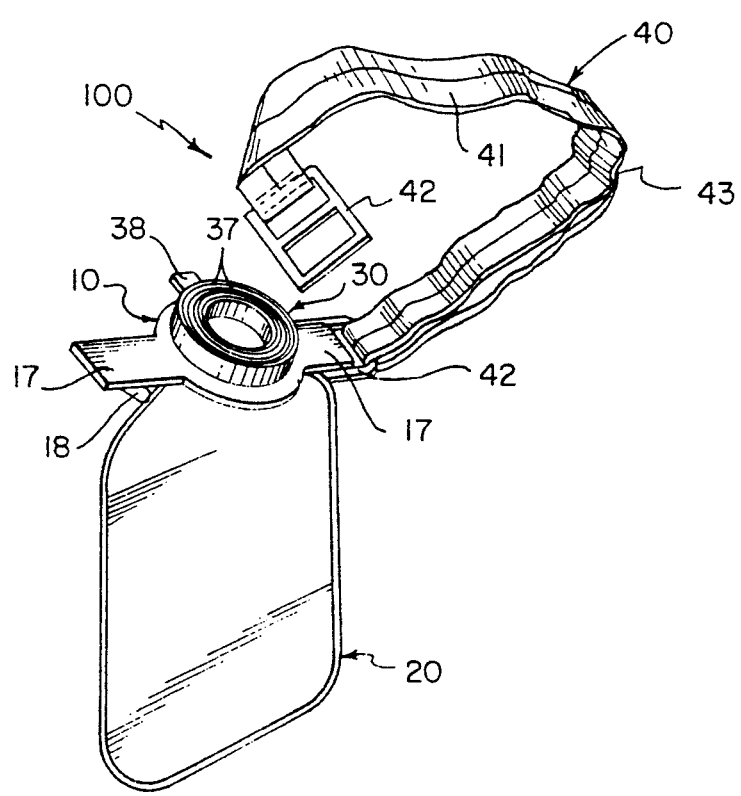
FIG. 2 is a perspective view of the complete appliance showing the pouch, the assembly base, the sealing surface of the sealing ring, and the adjustable elastic belt.

Referring still to FIGS. 1 and 2, the adjustable elastic belt 40 is shown to comprise an elastic band or webbing 41 of a length suitable to accommodate the torsos of patients of various sizes. A conventional adjusting slide of the type used on ordinary belts is provided to adjust the belt to the torso of the individual wearer. The slide is not shown in detail but is only indicated at 43 in FIG. 2. Each end of the belt is provided with a fastener or ring 42 for engaging lugs 18 of the assembly base. The fasteners 42 can be formed of metal or a synthetic plastic material such as polycarbonate. The webbing 41 may be any elastic textile material commonly employed in belts.

Turning now to FIGS. 3–5, these figures illustrate the assembly base 10 in detail. The entire assembly base 10 is of one-piece construction and is made of a soft, supple, flexible, elastomeric material. The preferred elastomeric material is a Food and Drug Administration approved thermoplastic rubber obtainable from Monsanto Corporation under the product designation Santoprene 281-64. However, other elastomers may be utilized. The assembly base 10 has a circular central portion 11 with a circular central aperture 12 extending completely therethrough. The central portion 11 also includes an upstanding circular boss having a peripheral groove 14 for purposes later to be described. Extending inwardly from the top surface 15 of the upstanding circular boss 13 is a circular V-shaped groove 16. This V-shaped groove 16 serves several important purposes. First, it reduces the mass of the molded elastomer constituting the upstanding circular boss 13 and thus decreases the molding time cycle. Secondly, it gives the entire central portion greater flexibility. Third, it makes it possible for the sealing ring 30 (FIGS. 6 and 7) to readily conform to the shape of the circular boss 13, thereby establishing a positive locking mode between those two parts. Lastly, it creates a space for receiving the O-ring in the embodiment described below which employs an O-ring in conjunction with the pouch top. Extending outwardly from the circular central portion 11 of the assembly base 10 at positions 180 degrees apart are two wing members 17. The underside of each wing member has a hook-shaped lug 18 for receiving the end fasteners or rings 42 of the adjustable elastic belt.

Reference is now made to FIGS. 6 and 7, which depict the sealing ring or stoma ring 30 in detail. The sealing ring 30 preferably is made of the same thermoplastic rubber material as the assembly base and thus has the same soft, supple, flexible, and elastomeric characteristics. Sealing ring 30 is circular in shape with a circular central opening or aperture 31, defined by an inner cylindrical rim 32, extending completely therethrough. Sealing ring 30 also has an outer peripheral cylindrical rim 33 which, with the inner cylindrical rim 32, defines a circular chamber 34 having an open entrance. The outer cylindrical rim 33 includes a circular lip 35 protruding into the chamber 34 at the entrance thereof for cooperation with the aforementioned peripheral groove 14 in the upstanding circular boss 13 of the assembly base 10. The top or body-confronting surface of the sealing ring 30 is planar and has formed thereinto by molding or cutting a plurality of closely spaced V-shaped circular grooves 36 arranged concentrically. These grooves 36 are precisely like a standard mechanical thread shape and thus produce concentric pointed thread-shaped formations 37. Since the body-confronting surface is flat and planar with the V-shaped grooves 36 molded or cut into it, the tips of the pointed thread-shaped formations 37 do not protrude beyond the top surface but instead all lie in the plane of the top surface. The effect of these V-shaped grooves 36 and resulting pointed thread-shaped formations 37 is the creation of a non-skid surface which prevents slippage of the sealing ring 30 when placed against the skin of the patient without causing undue irritation. The exact number and size of the V-shaped grooves is not critical, but it was found through experimentation that several grooves of small size caused significantly less irritation to the skin than did fewer grooves of larger size. For best results and least irritation, the optimum number of V-shaped grooves 36 appears to be eight, with the resulting pointed thread-shaped formations 37 then being seven. The preferred depth of the V-shaped grooves 36 is 0.040 inch, but again this exact depth is not critical. When the sealing ring 30 is in place surrounding the stoma, an extremely high quality seal is achieved by the V-shaped grooves 36 and pointed thread-shaped formations 37 without skin irritation.

The sealing ring 30 also includes a pulling tab 38 extending from outer rim 33 for assisting in detaching it from the assembly base 10 when installing a clean, empty pouch. The pulling tab also has another function explained below in connection with FIG. 14.

The pouch 20 is a thin flexible elongated plastic bag formed of FDA approved polyvinyl chloride or other suitable plastic material and, except for various specialized top configurations, is of the sort typically utilized in enterostomy appliances. The bottom portion of the pouch may be permanently closed, as illustrated in FIGS. 1 and 2, or arranged for dumping; but the particular style of the bottom portion is not important because it is not a factor of the present invention. The construction of the top portion is important, however, and three different top configurations have been found to be particularly effective.

Figure 8A:
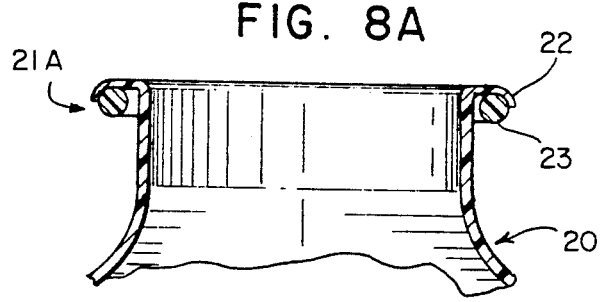
FIG. 8A is a cross-sectional view of a first pouch top configuration, which includes an O-ring.
Figure 8B:
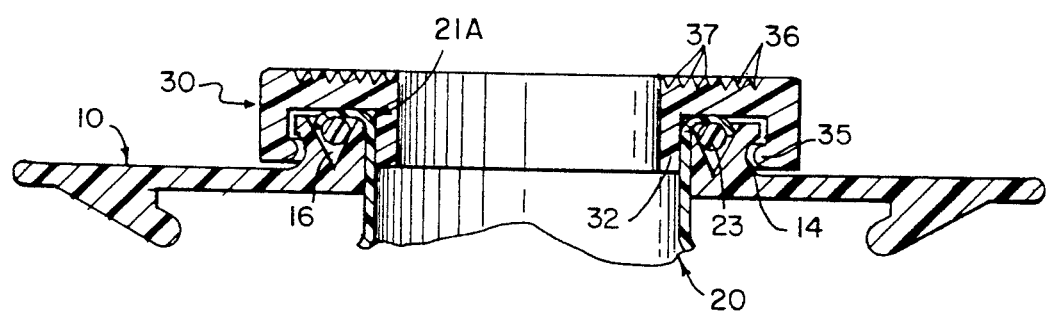
FIG. 8B is a cross-sectional view of the first pouch top configuration captivated between the assembly base and the sealing ring.

A first pouch top configuration is shown in FIG. 8A and is designated 21A. In this configuration the top extremity of the pouch is turned outwardly to form a curved flange 22. Flange 22 on its underside is sonically welded or adhesively attached to an O-ring 23. This top configuration can then be inserted through the central aperture 12 of the assembly base 10 with the O-ring 23 seated in the V-shaped groove 16 where it is captivated by the sealing ring 30, all as clearly shown in FIG. 8B. Sealing ring 30 is maintained in place on the assembly base 10 by the lip 35 snapping into groove 14. This top configuration is especially advantageous to the user because the top end of the pouch with the attached O-ring 23 will immediately fall into the right position within the assembly base when installing the pouch. Hence, initial placement as well as replacement of the pouch becomes a simple procedure requiring little manual dexterity and only a few moments time.

Figure 9A:
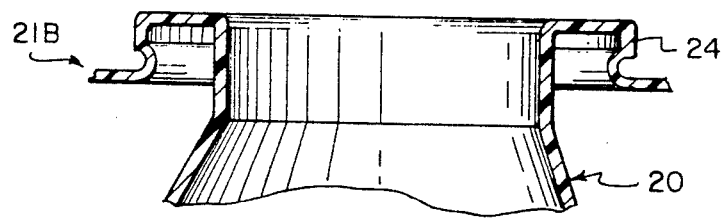
FIG. 9A is a cross-sectional view of a second pouch top configuration.
Figure 9B:
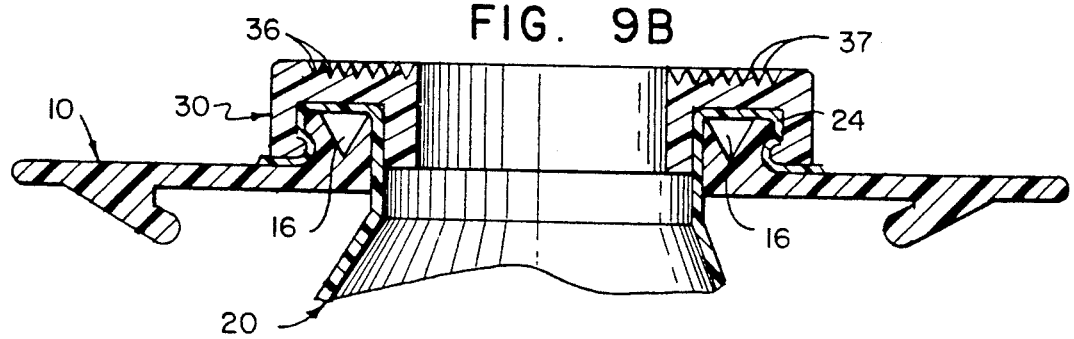
FIG. 9B is a cross-sectional view of the second pouch top configuration captivated between the assembly base and the sealing ring.

A second pouch top configuration 21B is shown in FIG. 9A. This configuration is the form which the pouch material assumes when the top portion of the pouch is inserted through the central aperture 12 of the assembly base, turned outwardly, and then pressed tightly against the upstanding circular boss 13 of the assembly base 10 by the sealing ring 30. As clearly shown in FIG. 9B, by captivating the turned-back top portion 24 of the pouch between the assembly base 10 and sealing ring 30, the top portion of the pouch takes the form of the inside shape of the sealing ring 30 and the outside shape of the upstanding circular boss 13 of the assembly base 10. Although slightly more time may be required to install the pouch of this embodiment than it takes with the other embodiments, nevertheless installation is still a simple procedure requiring little effort.

Figure 10A:
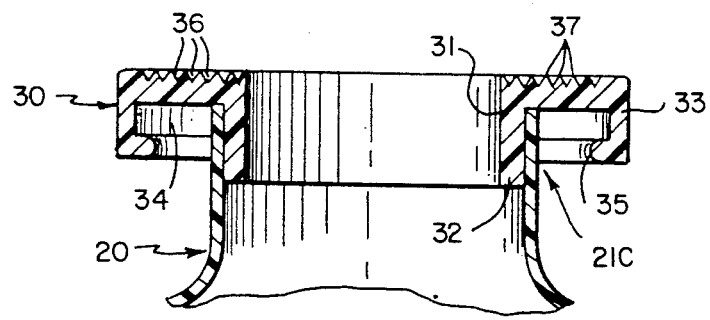
FIG. 10A is a cross-sectional view of a third pouch top configuration attached to the sealing ring.
Figure 10B:
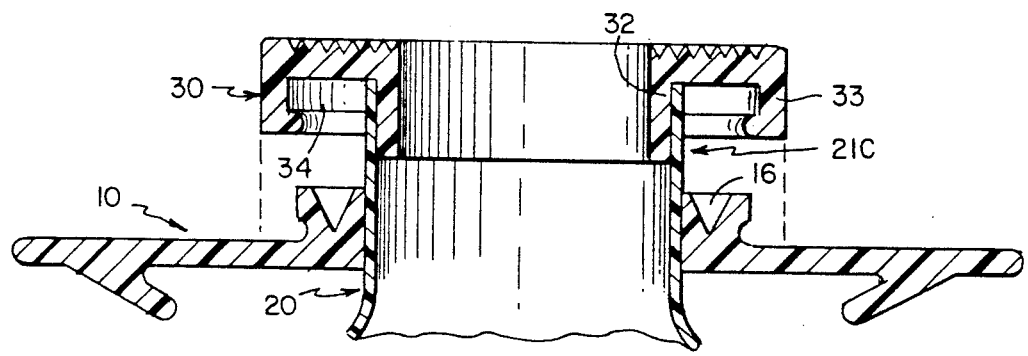
FIG. 10B is a cross-sectional view of the third pouch top configuration and attached sealing ring assembled with the assembly base.

A third pouch top configuration 21C is shown in FIG. 10A. In this embodiment the top of the pouch is sonically welded or adhesively attached to the inner cylindrical rim 32 of the sealing ring 30, thus, in effect, making the sealing ring an integral part of the pouch. In this situation, in order to install the pouch with the assembly base 10, it is necessary to feed the bottom of the pouch through the central aperture 12 of the assembly base, as indicated in FIG. 10B. Once again, the procedure for installing the pouch is extremely simple and can be accomplished quickly.

Although not essential, it is preferred when employing the third pouch top configuration that the inner cylindrical rim 32 of the sealing ring 30 be made slightly longer than the outer cylindrical rim 33 in order to facilitate sonic welding or adhesive securement of the pouch top thereto. The slightly longer length is depicted in FIGS. 10A and 10B.

In all three embodiments the pouch is securely held against accidental dislodgement when the sealing ring 30 is coupled with or fitted to the assembly base 10.

Figure 11:
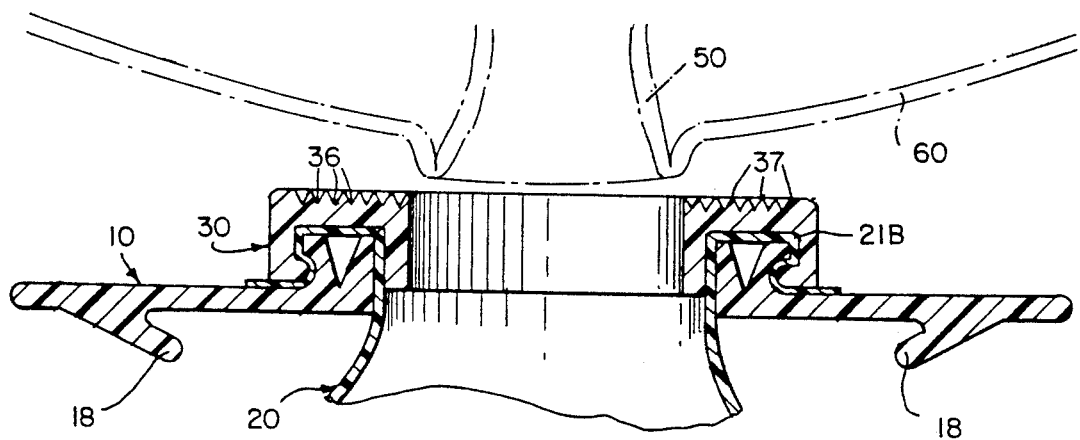
FIG. 11 is a cross-sectional view of an assembled appliance in position for placement against the abdominal wall surrounding a stoma, portions of the abdominal wall and stoma being shown in phantom.
Figure 12:
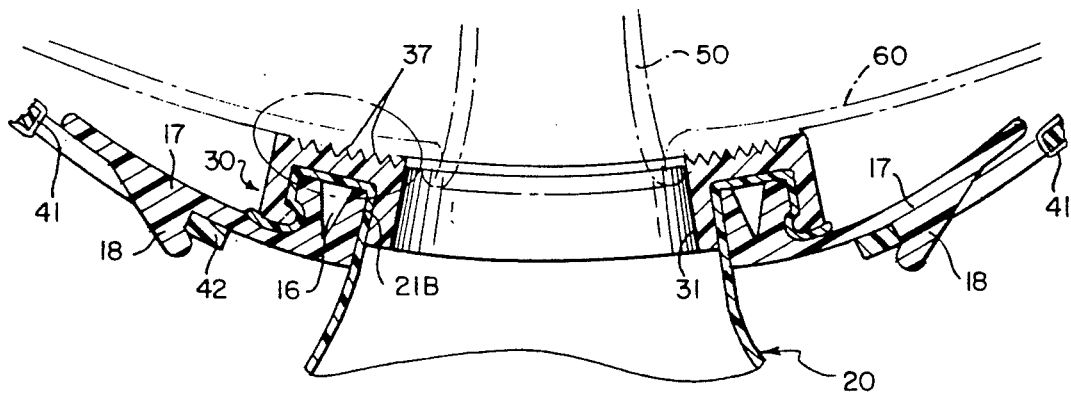
FIG. 12 is a cross-sectional view similar to FIG. 11 but showing the appliance in place against the abdominal wall.
Figure 13:
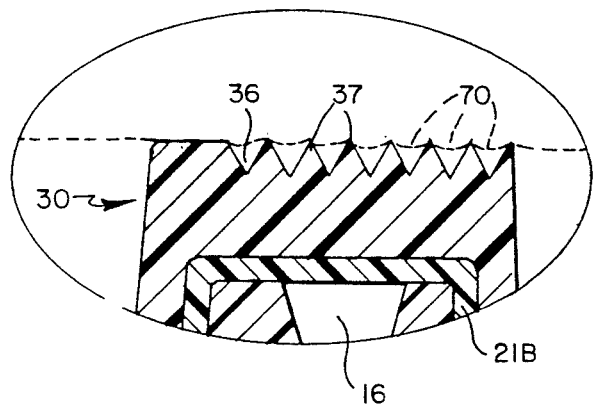
FIG. 13 is an enlarged detail view of the portion of the appliance indicated by the dashed line oval in FIG. 12 illustrating the manner in which the skin, shown in phantom, enters into the spaces between the thread-shaped rings of the sealing ring.

With reference now to FIGS. 11 and 12, the manner of attaching the entire appliance to a patient is explained. Once a pouch with any one of the three previously described top configurations is installed with the assembly base 10, the entire unit composed of assembly base 10, pouch 20, and sealing ring 30 is brought into position adjacent the patient's abdominal wall 60 at the stoma 50, as illustrated in FIG. 11. The adjustable elastic belt 40 is then placed around the patient's torso and the two fastener rings 42 of the belt are engaged with the two hook-shaped lugs 18 of the assembly base. The belt is adjusted as needed and the sealing ring is carefully positioned so that the central aperture 31 thereof is centered over the stoma, all as clearly shown in FIG. 12. The tension applied to the assembly base 10 by the belt 40 causes the wings 17 to curve about the patient's body and the sealing ring 30 to conform to the natural shape of the patient's body. As a result, the pointed thread-shaped formations 37 produced by the V-shaped grooves 36 formed into the body-confronting surface of the sealing ring 30 press tightly against the skin 70 of the patient and cause the skin to enter slightly into the grooves 36 in the manner shown in the enlarged detail view of FIG. 13. The result is a very efficient, leakproof seal extending entirely around the stoma which is non-irritating to the skin.

It should be noted that no adhesive or other sealing medium is needed in conjunction with the sealing ring 30 to achieve a reliable seal with the body of the wearer. The soft, supple, flexible, elastomer from which the sealing ring is made is pliable enough to respond immediately to body or muscle movements and yet firm enough to maintain a leakproof contact against the skin.

Figure 14:
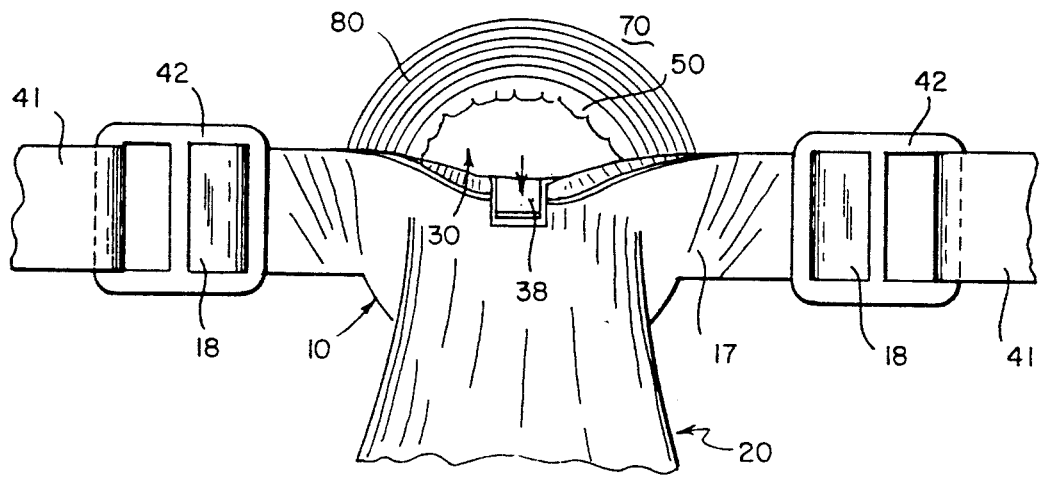
FIG. 14 is a frontal view of the appliance illustrating how it may be partially drawn away from the stoma to release gas.

Attention is now directed to FIG. 14, which illustrates another significant feature of the appliance. Occasions arise when flatus emanates from the stoma and accumulates in the pouch. Often it is desirable to be able to exhaust such flatus to the atmosphere. Because the sealing ring 30 of the invention needs no adhesive to effect a reliable seal, it becomes a simple matter to quickly release flatus. This is accomplished by simply grasping the pulling tab 38 on the sealing ring and partially bending the sealing ring back away from the skin in the manner shown in FIG. 14. As soon as the flatus is released, the sealing ring is allowed to return to its sealing position. This procedure for releasing flatus can be performed unobtrusively and without removing loose clothing.

FIG. 14 also shows impressions 80 which are left on the skin by the pressure exerted by the pointed thread-shaped formations 37. These impressions are entirely harmless and are akin to the impressions left on the skin after removal of a tightly fitting undergarment or wristwatch. They are indicative of the highly reliable seal attained by the action of the V-shaped grooves 36 and pointed thread-shaped formations 37.

It should be understood that the component parts of the appliance need not have the exact shapes and constructions shown in the drawings but are capable of slight variations such as would readily occur to one of ordinary skill in the art. For instance, neither the central aperture 12 of the assembly base nor the central aperture 31 of the sealing ring need be precisely circular but could be other annular shapes. However, a circular shape is preferred. Likewise, neither the upstanding boss 13 nor the sealing ring 30, including its chamber 34, need be strictly circular but could be other annular shapes. Again, however, the circular shape is preferred.

Similarly, the end fasteners 42 of the belt could be hooks or other simple fastening elements rather than ring members, in which case the lugs 18 on the wings 17 would be modified appropriately. These and other such obvious modifications fall within the scope of the invention which is limited not by the precise illustrations of the drawing but only by the terms of the claims.

It is further to be noted that while the various parts of the enterostomy appliance have been expressed in terms of their specific structures throughout the above description, as an alternative they may be expressed in terms of their specific functions. For example, the assembly base 10 in its entirety can be expressed as a means for carrying or mounting the pouch and sealing ring. Similarly, the assembly base 10 together with the sealing ring 30 may be termed a means for retaining the pouch. Likewise, the sealing ring can be defined as a means for establishing a fluid-tight seal with the skin. Further, the belt 40 can be expressed as a means for encircling the torso and maintaining the pouch, sealing ring and assembly base in proper position on the wearer's body. Further still, the pouch can be defined as a means for receiving discharges from the body or as a means for receiving body effluent. Finally, the pulling tab 38 in addition to being expressed as a means for assisting in detaching the sealing ring 30 from the assembly base 10, can also be expressed as constituting a means for grasping and drawing the sealing ring away from the wearer's skin to release flatus, or, even more simply, as a means to relieve flatus. Other elements may be expressed in similar fashion.

From the foregoing description, it is apparent that the enterostomy appliance of the invention fulfills all of the objects listed above, meets a long-felt need, and overcomes the deficiencies of the prior art appliances.

I claim:

1. An enterostomy appliance, comprising: a flexible pouch having an open end for placing in position over a stoma formed in a person's abdominal wall for receiving feces and other effluent discharged from the person's body through the stoma, and having a closed opposite end; a flexible sealing ring for forming a seal at the stoma; and an assembly base carrying the pouch and the sealing ring; said sealing ring being in the form of an annular member having a central aperture for receiving the stoma and a planar body-confronting surface encircling the central aperture for establishing a fluid-tight seal with the skin of the person's body in the area immediately surrounding the stoma, a plurality of closely spaced V-shaped annular grooves formed into said annular member from said planar body-confronting surface thereof, said V-shaped annular grooves being concentric with each other and with said central aperture, the spacing between adjacent V-shaped annular grooves being such that an annular pointed thread-shaped formation terminating in a tip is formed between each two adjacent grooves, each annular pointed thread-shaped formation being concentric with said V-shaped annular grooves, with each other, and with said central aperture, and the tips of all said annular pointed thread-shaped formations lying in the plane of the body-confronting surface of said annular member.

2. The enterostomy appliance in accordance with claim 1 wherein the sealing ring is formed of a soft, supple, flexible elastomer which is pliable enough to respond immediately to body or muscle movement and yet firm enough to maintain a fluid-tight contact against the skin.

3. The enterostomy appliance in accordance with claim 1 wherein the assembly base comprises an annular central portion including a centrally positioned upstanding annular boss, said upstanding annular boss having a top surface and an external peripheral groove located slightly below the top surface, and a substantially circular central aperture extending from said top surface of said upstanding annular boss through the entire annular central portion.

4. The enterostomy appliance in accordance with claim 3 wherein the sealing ring has an inner cylindrical rim and an outer cylindrical rim both extending in the direction opposite from said body-confronting surface and defining therebetween an annular chamber with an open entrance, an annular lip extending from a surface of said outer cylindrical rim into said annular chamber at the entrance thereof, said annular lip interfitting with said peripheral groove of said upstanding annular boss of said assembly base and thereby coupling the sealing ring to the assembly base.

5. The enterostomy appliance in accordance with claim 4 wherein said top surface of said upstanding annular boss is planar and an annular V-shaped groove extends into said upstanding annular boss from said planar top surface thereof, said annular V-shaped groove being concentric with said substantially circular central aperture.

6. The enterostomy appliance in accordance with claim 5 wherein the open end of the pouch is turned outwardly to form a flange and an O-ring is attached to the underside of the flange, said flange being captivated between said sealing ring and said assembly base with the O-ring seated in said annular V-shaped groove in the planar top surface of said upstanding annular boss.

7. The enterostomy appliance in accordance with claim 4 wherein the open end of the pouch is turned outwardly and captivated between the inside surface of said annular chamber of said sealing ring and the outside surface of said upstanding annular boss.

8. The enterostomy appliance in accordance with claim 4 wherein the open end of the pouch receives said inner cylindrical rim of said sealing ring and is permanently secured thereto.

9. The enterostomy appliance in accordance with claim 8 wherein the permanent securement of the pouch to the inner cylindrical rim is a sonic weld.

10. The enterostomy appliance in accordance with claim 8 wherein the permanent securement of the pouch to the inner cylindrical rim is an adhesive connection.

11. The enterostomy appliance in accordance with claim 1 and further comprising an elastic belt for encircling the person's torso and for holding the pouch, sealing ring and assembly base in position on the person's body.

12. The enterostomy appliance in accordance with claim 11 wherein the assembly base includes two wing members positioned 180 degrees apart, each wing member having a hook-shaped lug for attachment of said elastic belt.

13. The enterostomy appliance in accordance with claim 1 wherein the sealing ring and the assembly base are both formed of identical soft, supple, flexible elastomeric material.

14. The enterostomy appliance in accordance with claim 1 wherein the sealing ring includes a pulling tab whereby it can be drawn away from the person's skin to release flatus.

15. An enterostomy appliance sealing ring for establishing a fluid-tight seal with the skin around the stoma of a person who has undergone an enterostomy, comprising: an annular member having a substantially circular central aperture extending completely therethrough, a planar top surface surrounding said substantially circular central aperture and extending the entire distance from said substantially circular central aperture to the perimeter of said annular member, and a plurality of closely spaced V-shaped annular grooves formed into said annular member from said planar top surface thereof, said V-shaped annular grooves being concentric with each other and with said substantially circular central aperture, the spacing between adjacent V-shaped annular grooves being such that an annular pointed thread-shaped formation terminating in a tip is formed between each two adjacent grooves, each annular pointed thread-shaped formation being concentric with said V-shaped annular grooves, with each other, and with said substantially circular central aperture, and the tips of all said annular pointed thread-shaped formations lying in the plane of said top surface; said annular member further including an inner cylindrical rim and an outer cylindrical rim both extending in the direction opposite from said planar top surface, each said inner cylindrical rim and said outer cylindrical rim having inner and outer cylindrical surfaces, the outer cylindrical surface of said outer cylindrical rim defining the outer periphery of said annular member and the inner cylindrical surface of said inner cylindrical rim being coincident with said substantially circular central aperture, the inner cylindrical surface of said outer cylindrical rim being spaced from the outer cylindrical surface of said inner cylindrical rim and defining an annular chamber having an open entrance, and an annular lip extending from the inner cylindrical surface of said outer cylindrical rim into said annular chamber at said open entrance thereof.

16. The enterostomy appliance sealing ring in accordance with claim 15 and further including a pulling tab extending outwardly from the outer cylindrical surface of said outer cylindrical rim.

17. The enterostomy appliance sealing ring in accordance with claim 15 formed entirely in one unitary piece from a soft, supple, flexible elastomer.

18. An enterostomy appliance assembly base for retaining component parts of an enterostomy appliance, comprising: an annular central portion including a centrally positioned upstanding annular boss, said upstanding annular boss having a peripheral groove and a planar top surface, a substantially circular central aperture extending from said planar top surface of said upstanding annular boss through the entire annular central portion, and an annular V-shaped groove extending into said upstanding annular boss from the planar top surface thereof, said annular V-shaped groove being concentric with said substantially circular central aperture.

19. The enterostomy appliance assembly base in accordance with claim 18 and further including two wing members extending outwardly from said annular central portion at positions 180 degrees apart.

20. The enterostomy appliance assembly base in accordance with claim 19 and further including a hook-shaped lug on the underside of each wing member.

21. The enterostomy appliance assembly base in accordance with claim 18 formed entirely in one unitary piece from a soft, supple, flexible elastomer.

22. An enterostomy appliance, comprising: a flexible pouch for placing in position over a stoma formed in a person's abdominal wall for receiving feces and other effluent discharged from the person's body through the stoma; a flexible annular sealing ring for establishing a fluid-tight seal with the person's skin in the area immediately surrounding the stoma, said sealing ring having a central aperture for receiving the stoma and for communicating with the interior of the pouch, and said sealing ring also having means for grasping and drawing the sealing ring away from the person's skin in order to release flatus accumulated in the pouch; and a flexible assembly base carrying the pouch and sealing ring; said means for grasping and drawing the sealing ring away from the person's skin being located externally of said pouch and protruding outwardly beyond said flexible assembly base.

23. The enterostomy appliance in accordance with claim 22 wherein the means for grasping and drawing the sealing ring away from the person's skin comprises a pulling tab.

24. An enterostomy appliance flexible sealing ring for establishing a fluid-tight seal with the skin around the stoma of a person who has undergone an enterostomy, comprising: an annular member formed entirely in one unitary piece from a soft, supple, flexible elastomeric material and having a central aperture for receiving the stoma, a planar body-confronting surface encircling said central aperture for establishing a fluid tight seal with the skin of the person's body in the area immediately surrounding the stoma, means opposite said planar body-confronting surface for receiving a portion of a flexible pouch, and a plurality of closely spaced V-shaped annular grooves formed into said annular member from said planar body-confronting surface thereof, said V-shaped annular grooves being concentric with each other and with said central aperture, the spacing between adjacent V-shaped annular grooves being such that an annular pointed thread-shaped formation terminating in a tip is formed between each two adjacent grooves, each annular pointed thread-shaped formation being concentric with said V-shaped annular grooves, with each other, and with said central aperture, and the tips of all said annular pointed thread-shaped formations lying in the plane of said body-confronting surface of said annular member.

25. An enterostomy appliance, comprising: a flexible pouch having an open end for placing in position over a stoma formed in a person's abdominal wall for receiving feces and other effluent discharged from the person's body through the stoma, and having a closed opposite end; a flexible sealing ring for forming a seal at the stoma; and an assembly base carrying the pouch and the sealing ring; said assembly base having an annular central portion including a centrally positioned upstanding annular boss, said upstanding annular boss having a peripheral groove and a planar top surface, a substantially circular central aperture extending from said planar top surface of said upstanding annular boss through the entire annular central portion, and an annular V-shaped groove extending into said upstanding annular boss from the planar top surface thereof, said annular V-shaped groove being concentric with said substantially circular central aperture.

26. The enterostomy appliance sealing ring in accordance with claim 24 and further including means extending outwardly from the perimeter of said annular member for grasping and drawing the sealing ring away from the person's skin.

* * * * *